US010424062B2

(12) United States Patent
Salvado et al.

(10) Patent No.: US 10,424,062 B2
(45) Date of Patent: Sep. 24, 2019

(54) REPRESENTING AN INTERIOR OF A VOLUME

(71) Applicant: Commonwealth Scientific and Industrial Research Organisation, Acton, Australian Capital Territory (AU)

(72) Inventors: Olivier Salvado, Acton (AU); Hans De Visser, Acton (AU); Cédric Dumas, Acton (AU)

(73) Assignee: Commonwealth Scientific and Industrial Research Organisation, Acton, Australian Capital Territory (AU)

( * ) Notice: Subject to any disclaimer, the term of this patent is extended or adjusted under 35 U.S.C. 154(b) by 61 days.

(21) Appl. No.: 15/501,648

(22) PCT Filed: Aug. 5, 2015

(86) PCT No.: PCT/AU2015/050445
§ 371 (c)(1),
(2) Date: Feb. 3, 2017

(87) PCT Pub. No.: WO2016/019439
PCT Pub. Date: Feb. 11, 2016

(65) Prior Publication Data
US 2017/0228861 A1    Aug. 10, 2017

(30) Foreign Application Priority Data
Aug. 6, 2014 (AU) .............................. 2014903053

(51) Int. Cl.
*G06K 9/00* (2006.01)
*G06T 7/00* (2017.01)
(Continued)

(52) U.S. Cl.
CPC .............. *G06T 7/0012* (2013.01); *A61B 1/04* (2013.01); *A61B 1/31* (2013.01); *G06T 7/11* (2017.01);
(Continued)

(58) Field of Classification Search
CPC ......... G06T 7/0012; G06T 7/11; G06T 7/149; G06T 7/74; G06T 3/00; G06T 5/006;
(Continued)

(56) References Cited

U.S. PATENT DOCUMENTS 6,106,466 A    8/2000  Sheehan et al.
6,201,543 B1 *  3/2001  O'Donnell ........... G06K 9/6207
                                                345/420
(Continued)

FOREIGN PATENT DOCUMENTS

EP    1 832 223 A1    9/2007
WO    2004/081873 A2  9/2004
(Continued)

OTHER PUBLICATIONS

International Search Report and Written Opinion of the International Searching Authority for corresponding International Patent Application No. PCT/AU2015/050445 dated Oct. 19, 2015, 10 pgs.
(Continued)

*Primary Examiner* — Jose L Couso
(74) *Attorney, Agent, or Firm* — Merchant & Gould P.C.

(57) ABSTRACT

This disclosure relates to representing an interior of a volume, such as but not limited to, a lumen. Examples of lumens may comprise a colon or bronchus. An input port receives the captured image data of the interior of the volume. The processor selects one of the multiple candidates such that the selected one of the multiple candidates corresponds to the captured image data. Each candidate is associated with simulated image data of the interior of the
(Continued)

volume. The processor stores an association of the selected candidate with the captured image data to represent the interior of the volume. Aspects of the disclosure include computer implemented methods, computer systems and software.

9 Claims, 17 Drawing Sheets

(51) Int. Cl.
| | |
|---|---|
| *G06T 19/00* | (2011.01) |
| *G06T 7/11* | (2017.01) |
| *G06T 7/149* | (2017.01) |
| *A61B 1/04* | (2006.01) |
| *A61B 1/31* | (2006.01) |

(52) U.S. Cl.
CPC .............. *G06T 7/149* (2017.01); *G06T 19/00* (2013.01); *G06T 2207/10068* (2013.01); *G06T 2207/20081* (2013.01); *G06T 2207/30028* (2013.01); *G06T 2207/30172* (2013.01); *G06T 2210/41* (2013.01)

(58) Field of Classification Search
CPC ... G06T 13/00–20; G06T 15/00; G06T 15/08; G06T 15/20; G06T 17/00; G06T 17/10; G06T 17/20; G06T 19/00; G06T 19/003; G06T 2200/00; G06T 19/04; G06T 19/08; G06T 2207/10068; G06T 2207/10072; G06T 2207/10076; G06T 2207/10081; G06T 2207/10124; G06T 2207/10136; G06T 2207/20081; G06T 2207/20108; G06T 2207/20221; G06T 2207/30004; G06T 2207/30028; G06T 2207/30032; G06T 2207/30048; G06T 2207/30056; G06T 2207/30061; G06T 2207/30081; G06T 2207/30084; G06T 2207/30092; G06T 2207/30096; G06T 2207/30101; G06T 2207/30104; G06T 2210/41; A61B 1/00; A61B 1/00002; A61B 1/00009; A61B 1/005; A61B 1/04; A61B 1/041; A61B 1/31; A61B 5/055; A61B 5/107; A61B 5/1075; A61B 5/4255; A61B 6/032; A61B 6/466; A61B 8/0833; A61B 8/466; A61B 8/467; A61B 8/483; A61B 8/5223; A61B 34/10; A61B 2090/364; G01S 7/52068; Y10S 128/916; Y10S 128/92; Y10S 128/922; Y10S 128/923; G06K 2209/40; H04N 13/275; H04N 21/8146; H04N 21/816; H04N 2213/005; G06F 19/321; G06F 19/3481; G09B 23/28; G09B 23/285; G16H 50/50

See application file for complete search history.

(56) References Cited

U.S. PATENT DOCUMENTS

| | | | | |
|---|---|---|---|---|
| 6,556,696 B1* | 4/2003 | Summers | ........... | G06K 9/00201 |
| | | | | 382/128 |
| 7,796,131 B2* | 9/2010 | Guendel | ................ | A61B 6/466 |
| | | | | 345/418 |
| 2001/0031920 A1* | 10/2001 | Kaufman | ................ | A61B 5/055 |
| | | | | 600/431 |
| 2003/0208116 A1* | 11/2003 | Liang | ..................... | A61B 5/055 |
| | | | | 600/407 |
| 2003/0234781 A1* | 12/2003 | Laidlaw | .................. | G06T 15/08 |
| | | | | 345/419 |
| 2004/0015070 A1* | 1/2004 | Liang | .................. | G06F 19/3481 |
| | | | | 600/407 |
| 2007/0014452 A1* | 1/2007 | Suresh | ................ | G06F 19/3481 |
| | | | | 382/128 |
| 2008/0033302 A1* | 2/2008 | Grady | ...................... | G06K 9/34 |
| | | | | 600/481 |
| 2010/0016658 A1* | 1/2010 | Zou | ........................ | G06T 7/0012 |
| | | | | 600/101 |
| 2010/0165087 A1* | 7/2010 | Corso | ...................... | G06K 9/32 |
| | | | | 348/65 |
| 2010/0309198 A1* | 12/2010 | Kauffmann | ............ | A61B 6/504 |
| | | | | 345/419 |
| 2011/0013815 A1* | 1/2011 | Gundel | .................. | A61B 5/055 |
| | | | | 382/128 |
| 2011/0063288 A1* | 3/2011 | Valadez | .................. | G06T 15/08 |
| | | | | 345/419 |
| 2011/0170752 A1* | 7/2011 | Martin | .................. | G09B 23/285 |
| | | | | 382/128 |
| 2011/0187707 A1 | 8/2011 | Kaufman et al. | | |
| 2012/0053408 A1 | 3/2012 | Miyamoto | | |
| 2012/0203067 A1 | 8/2012 | Higgins et al. | | |
| 2012/0316421 A1* | 12/2012 | Kumar | ............... | A61B 1/00009 |
| | | | | 600/407 |
| 2013/0113802 A1* | 5/2013 | Weersink | ................ | G06T 15/20 |
| | | | | 345/427 |
| 2014/0232719 A1* | 8/2014 | Wahrenberg | .......... | G06T 15/506 |
| | | | | 345/424 |
| 2014/0364739 A1* | 12/2014 | Liu | ....................... | A61B 8/5223 |
| | | | | 600/449 |
| 2016/0078625 A1* | 3/2016 | Tajbakhsh | ............. | G06T 7/0012 |
| | | | | 382/128 |
| 2016/0217573 A1* | 7/2016 | Lian | .......................... | G06T 5/20 |
| 2017/0046835 A1* | 2/2017 | Tajbakhsh | ............. | G06T 7/0012 |

FOREIGN PATENT DOCUMENTS

| | | | | |
|---|---|---|---|---|
| WO | WO-2012028190 A1 * | 3/2012 | ............ | G06T 17/00 |
| WO | 2012/156873 A1 | 11/2012 | | |

OTHER PUBLICATIONS

Szpala, S. et al., "Real-Time Fusion of Endoscopic Views With Dynamic 3-D Cardiac Images: A Phantom Study", IEEE Transactions on Medical Imaging, 24(9): 1207-1215 (2005).

Xue, H. et al., "Three-dimensional echocardiographic virtual endoscopy for the diagnosis of congenital heart disease in children", Int. J. Cardiovasc Imaging, 26(8): 851-859 (2010).

Extended European Search Report for corresponding European Patent Application No. 15829049.4 dated Jan. 3, 2018, 9 pages.

DeVisser, H. et al., "Developing a Next Generation Colonoscopy Simulator", International Journal of Image and Graphics, 10(2): 203-217 (2010).

* cited by examiner

1000

REPRESENTING AN INTERIOR OF A VOLUME

CROSS-REFERENCE TO RELATED APPLICATIONS

This application is a National Stage Application of PCT/AU2015/050445 filed on 5 Aug. 2015, which claims priority from the Australian provisional application 2014903053 filed on 6 Aug. 2014 with Commonwealth Scientific and Industrial Research Organisation being the applicant and the contents of which are incorporated herein by reference. To the extent appropriate, a claim of priority is made to each of the above disclosed applications.

TECHNICAL FIELD

This disclosure relates to representing an interior of a volume, such as but not limited to, a lumen. The disclosure includes a computer implemented method, a computer system and software.

BACKGROUND

The human colon is prone to a number of diseases, the most prominent of which is colorectal cancer, which is estimated to kill around 600,000 people annually worldwide.

Colonoscopy is considered the most effective diagnostic examination for colorectal cancer. A colonoscopy is a type of endoscopy that involves navigating a flexible endoscope through a very flexible organ and is difficult to master. Often, clinicians may miss polyps or areas of the colon hidden behind the colon (haustral) folds. It usually requires hundreds of cases before a physician is regarded as proficient enough to conduct the procedure without supervision. Most of this training currently occurs in real patients, causing increased patient risks and discomfort.

Computer based simulation is emerging as an alternative for at least a part of the training because it has lower costs, provides no risks to the patient and has the ability to efficiently structure the training program, allow trainees to make mistakes and learn from them, and expose them to rare scenarios.

SUMMARY

A computer implemented method for representing an interior of a volume, comprising:

receiving captured image data of the interior of the volume;

selecting one of multiple candidates such that the selected one of the multiple candidates corresponds to the captured image data, each candidate being associated with simulated image data of the interior of the volume; and storing an association of the selected one of the multiple candidates with the captured image data to represent the interior of the volume.

It is an advantage that an interior volume can be represented based on simulated image data which provides an alternative representation of the interior of the volume.

It is a further advantage that by selecting a candidate to represent the interior of a volume more can be known about the volume, since additional information known about the candidate is also information relevant to the volume.

Selecting one of the multiple candidates may comprise comparing the captured image data to each of the multiple candidates.

The method may further comprise:

determining a representation of one or more distinguishing features of the captured image data, wherein selecting the one of the multiple candidates is based on the representation of one or more distinguishing features of the captured image data.

Selecting one of the multiple candidates may comprise comparing the representation of one or more distinguishing features of the captured image data to each of the multiple candidates.

Each candidate may be associated with simulated image data representing a unique interior of a volume based on a parametric model.

The parametric model may represent the three-dimensional geometry of the volume and the captured image data and the simulated image data are represented in two dimensions.

The candidate may be associated with parameter values of the parametric model.

The candidate may be associated with simulated image data based on the parametric model.

The candidate may be associated with a representation of one or more distinguishing features of the simulated image data.

The candidate may be associated with multiple representations of the one or more distinguishing features. For example, the multiple representations represent the simulated image data at different rotations.

Selecting one of the multiple candidates may comprise comparing the representation of one or more distinguishing features of the captured image data to the representation of one or more distinguishing features of the simulated image data of each the multiple candidates.

The selected one of the multiple candidates may correspond to the captured image data by having substantially greater similarity with the captured image data than compared to similarity of the other of the multiple candidates to the captured image data.

The stored association of the one of the multiple candidates with the captured image data may comprise storing a copy of or pointer to parameters of the model.

The stored association may further comprise camera orientation data, and simulated image data based on the parameters of the model.

Selecting one of the multiple candidates comprises initially:

selecting one of multiple intermediary candidates, each intermediary candidate being associated with simulated image data of the interior of the volume such that the selected one of the multiple intermediary candidates corresponds to the captured image data; and determining the multiple candidates based on the selected one of the multiple intermediary candidates wherein the selected one of the multiple candidates corresponds to the captured image data by having substantially greater similarity with the captured image data than compared to similarity of the selected one of the multiple intermediary candidates to the captured image data.

The interior volume may be an interior of an anatomical volume. The interior volume may be a lumen.

The captured image data may be captured by a camera. The image may be a frame of a video. The method may be repeated for multiple captured image data.

The method may be substantially performed in real time.

Software, being computer readable instructions, that when performed by a computer system causes the computer system to perform the method of any one of the preceding claims.

A computer system to represent an interior of a volume, the computer system, comprising:

an input port to receive captured image data of the interior of the volume;

a processor to select one of multiple candidates, each candidate being associated with simulated image data of the interior of the volume such that the one of the selected multiple candidates corresponds to the captured image data; and memory to store an association of the selected one of the multiple candidates with the captured image data to represent the interior of the volume.

BRIEF DESCRIPTION OF DRAWINGS

Features of the present disclosure are illustrated by non-limiting examples, and like numerals indicate like elements, in which.

BEST MODE FOR CARRYING OUT THE INVENTION

Figure 1:
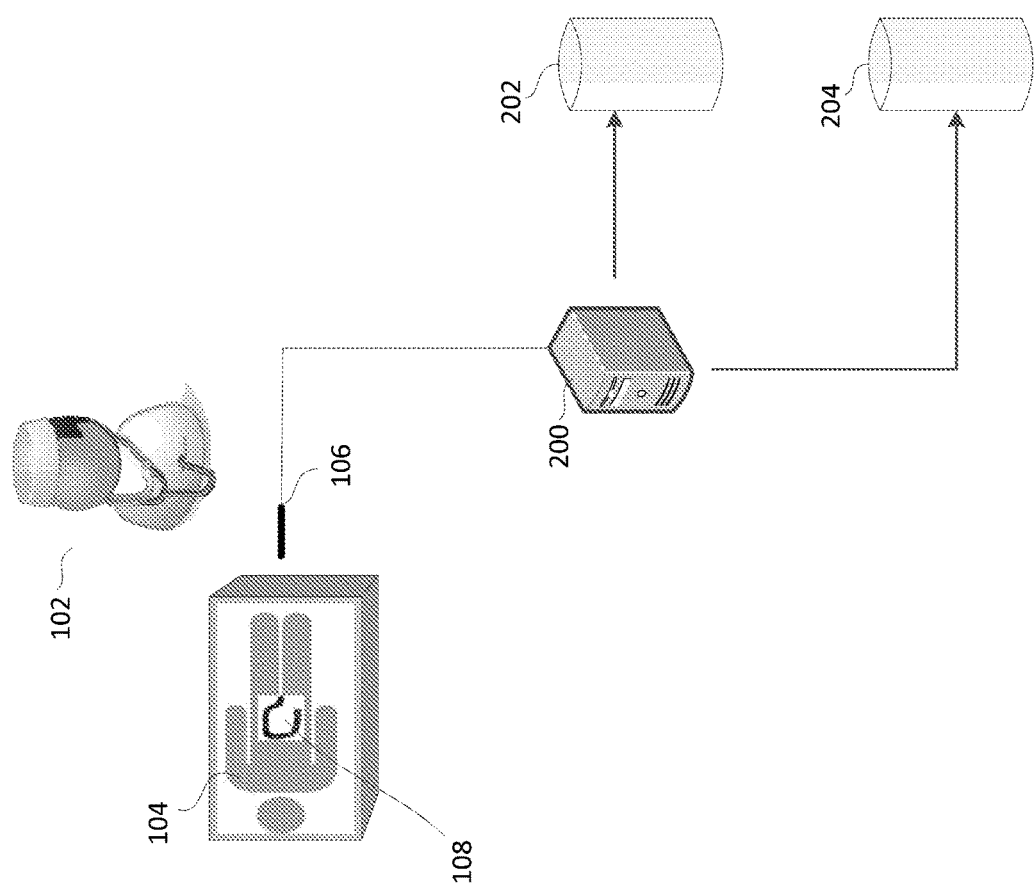
FIG. 1 is a diagram of an example computer system for representing an interior of a volume, which in this example is a colon.

FIG. 1 illustrates an example comprising a surgeon 102 who is to perform a colonoscopy of colon 108 of patient 104 using an endoscope device 106, such as a colonoscope. A colonoscopy more generally is the imaging of an interior of a volume, that is, the interior of the colon. It is to be noted that the following explanation equally applies to other endoscopies of other lumen. The endoscope 106 includes a camera (not shown) to capture a video of the interior of the colon. The video is received by the computer system 200 that is connected to a video database 202 where the video is stored.

The computer system 200 is further connected to a simulator database 204 that stores multiple unique predetermined candidates associated with simulated image data of the interior of the colon as will be described in detail below.

Figure 2:
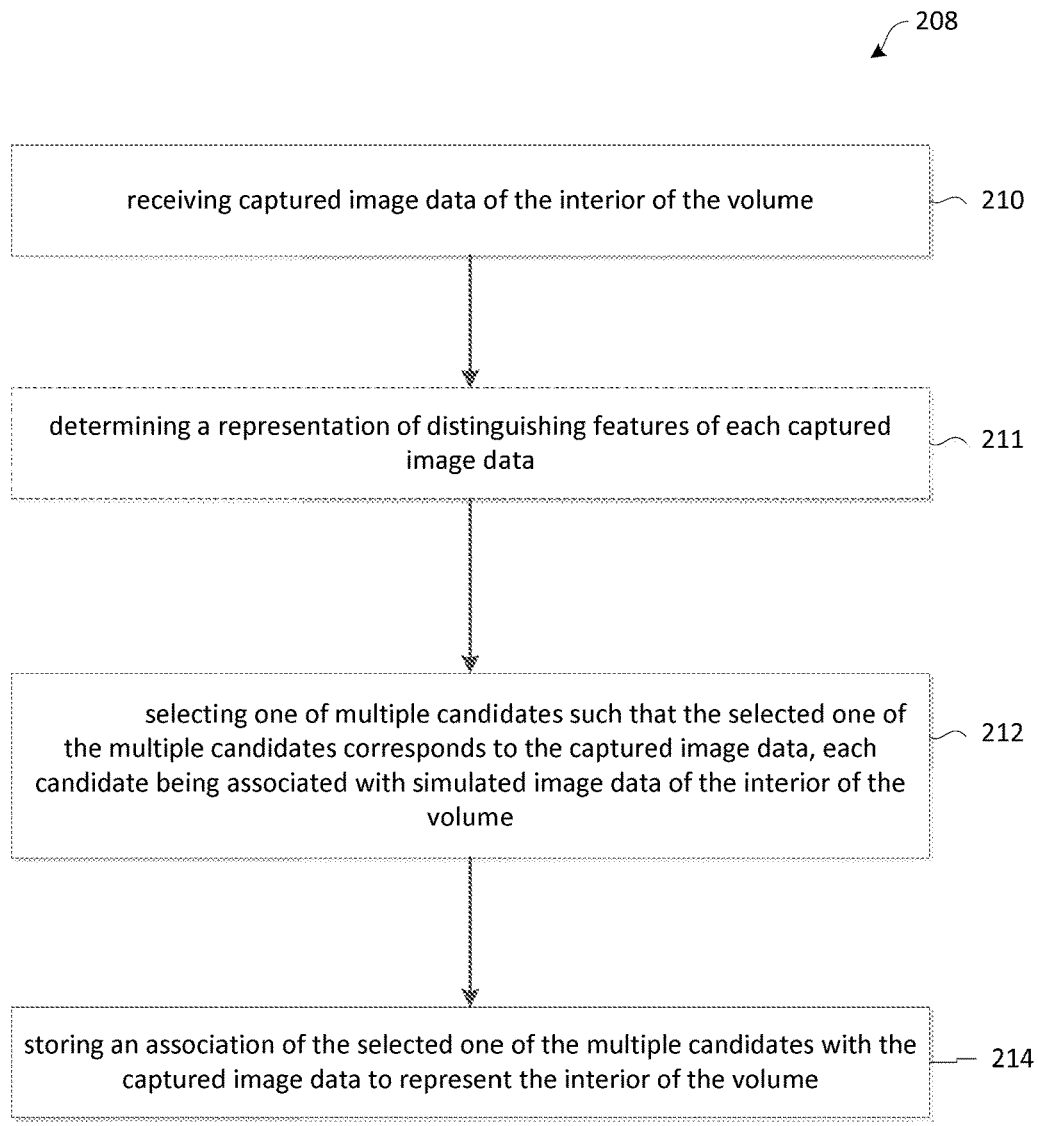
FIG. 2 is a flow chart of an example method for representing the interior of a volume.

The method 208 of FIG. 2 can be regarded as the testing phase. The computer system 200 receives one or more images, referred to here as captured image data, from an endoscopic video of the colon 210, and stores the captured image data in the video database 202.

The system 200 then selects one of multiple candidates stored in database 204, each candidate being associated with simulated image data of the interior of the colon as will be described with reference to FIG. 3. The selected one of the multiple candidates corresponds to the captured image data. Step 212 is repeated for multiple captured images of the video stored in the database 202.

Then, the method comprises storing an association of the selected one of the multiple candidates with the captured image data to represent the interior of the colon 214. Storing the association may comprise writing an identifier, such as an index, of the candidate or writing the distinguishing features in the same row of the video database 202 as the captured image.

Figure 3:
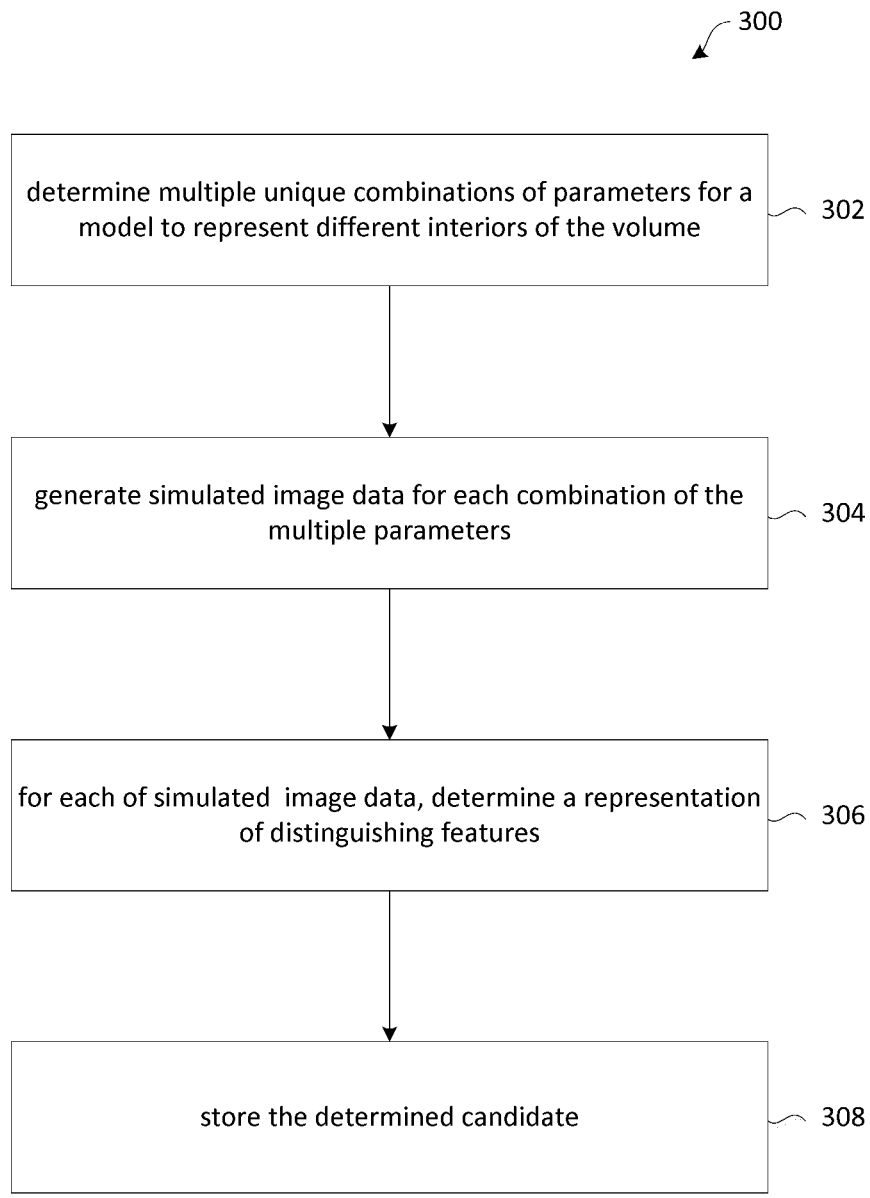
FIG. 3 is a flow chart of an example method for determining candidates each associated with simulated image data of the interior of the volume.

Initially before the testing phase 208, a method 300 that can be regarded as a training phase is performed as shown in FIG. 3. At the end of the training phase, the multiple candidates are determined and stored in the database 204. This method 300 is described as being performed by computer system 200 but can equally be performed by any other suitable computer system.

The training phase of FIG. 3 and the testing phase of FIG. 2 will now be described in more detail.

Training Phase

Figure 4A:
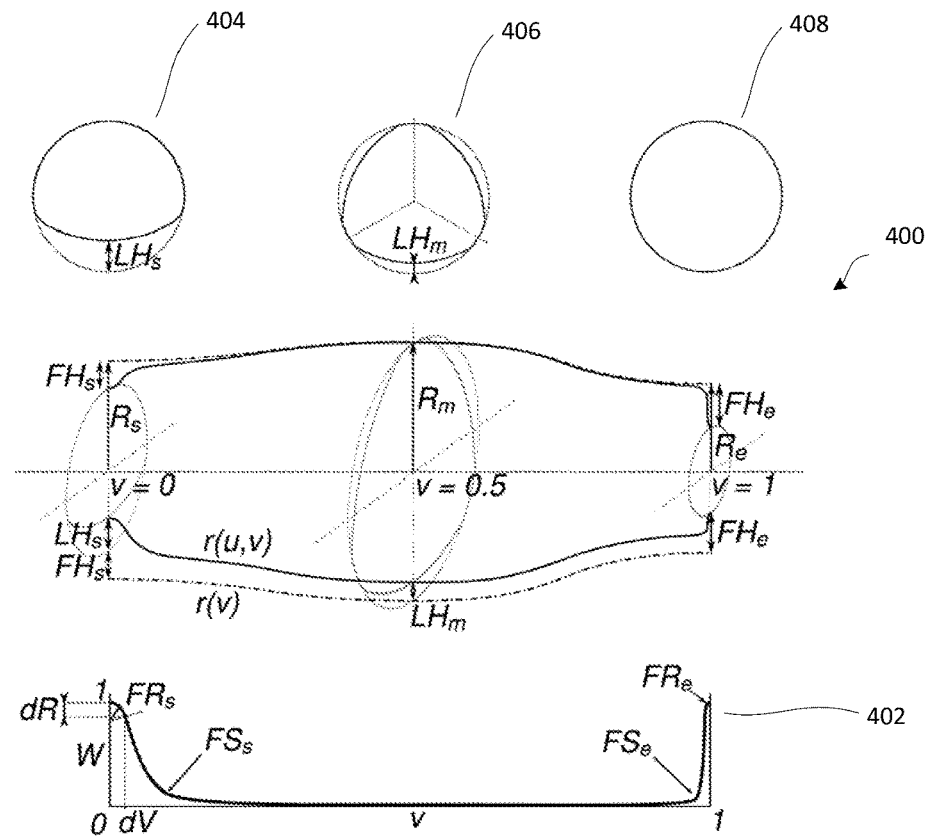
FIG. 4a illustrates schematically an example parametric model to represent the interior of a colon.

Referring first to the training phase, initially the system 200 determines multiple candidates. Each candidate is associated with simulated image data of the interior of the volume. In this example the system 200 uses a parametric model to model the internal three-dimensional geometry of a sub-part of the colon, such as that graphically shown in FIG. 4a. Simulated image data refers to image data that is computer generated based on parameters of the model, that is, the image data simulates what the camera at a specific location and orientation would capture of a particular part of the volume as defined by given parameter values. This generation process is similar to rendering a landscape in computer graphics with a given geometry and texture information. As such, similar to what is captured by the camera the simulated image data may be two-dimensional while the geometrical model describes a three-dimensional object.

To generate multiple candidates the system 200 iteratively progresses through multiple valid combinations of parameters of the parametric model and each unique combination of parameters forms the basis for a unique representation of the interior of the colon. For example, the system iterates over five possible values for the radius of the volume to generate five candidates. It is noted that the simulated image data may not be kept on the database 204 but only the model parameters and features as described later. Nevertheless, the candidates are still associated with simulated image data since each candidate is generated based on the simulated image data as explained below.

Figure 5:
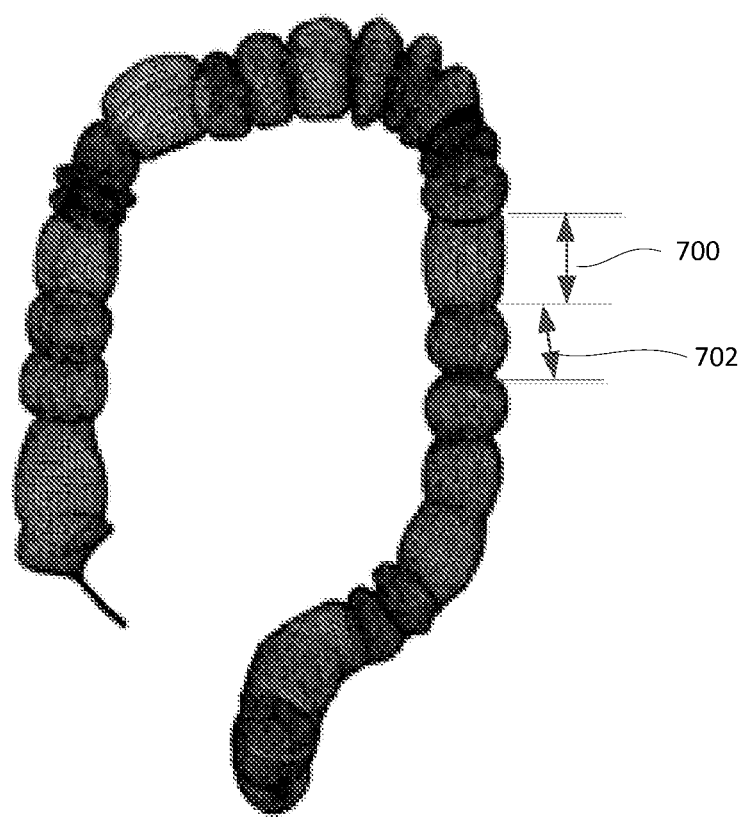
FIG. 5 schematically illustrates example chambers that comprise a colon.

In the example of a colonoscopy, the volume can be understood as a series of connected chambers constructed as a chain along a centre line. FIG. 5 shows two adjacent chambers 700 and 702.

Accordingly, the parametric model of this example defines a single chamber. The set of mathematical equations that comprise the parametric model of a chamber approximates important general structural features of the surface of the chamber, such as the internal surface and shape.

Figure 4B:
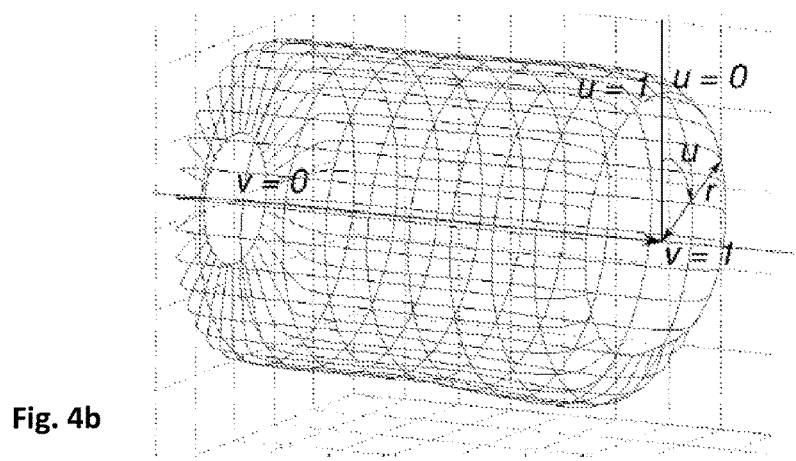
FIG. 4b is an example schematic representation of a cylindrical coordinate system that forms basis for the multiple candidates where the volume is a colon.

As shown in FIG. 4b, the set of equations that fully define a chamber's geometry consist of the description of the longitudinal profile 402, and the cross-sectional profiles of the start 404, middle 406 and end 408 of the chamber, noting that the fold at the end of the chamber is in fact the same as the starting fold of the adjacent chamber. Although this example is specific to a colon, a similar parametric model can be applied to any type of volume.

Each chamber is defined as a cylinder with a varying radius: each point on the surface of the chamber's wall can be described by the 3 coordinates u, v and r. Referring to r is the distance from the point to the centreline of the cylinder, v is the distance along this centreline and u is the circumferential coordinate, see FIG. 4a. The cylindrical surface, relative to the centreline, is therefore fully described by the function r(u,v,D,E) where D is a set of design parameters, which define the geometry of the chamber and contain properties such as the height and sharpness of the haustral fold. E is a set of environment parameters, such as colon insufflation and contact points, which causes temporary deformations to the geometry. The centreline itself, around which the surface sits, can deform as well, driven by some physically based model. However, the shape of the centreline is irrelevant for the design of the chamber, and is therefore assumed straight in the first design phase.

Design of the chamber shape is done in two steps: First, the cross-section of the chamber is defined at the start, the middle and the end. These cross-sections are referred to as the start, middle and end ring respectively. Secondly, the length profile, the transition from one ring to the next, is defined.

Figure 6:
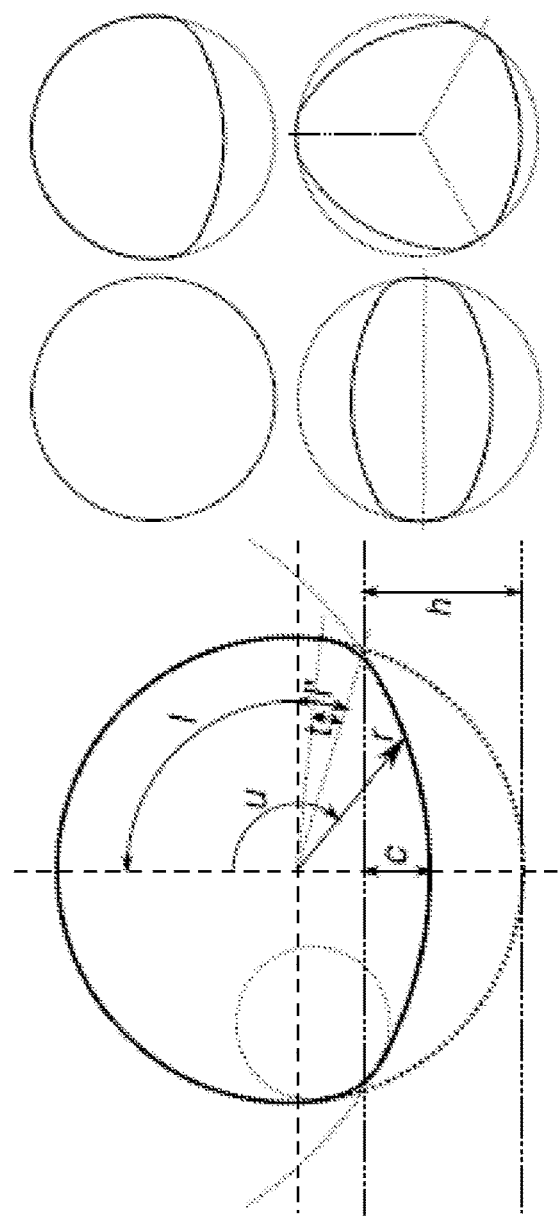
FIG. 6 is an example schematic representation of the cross-sectional profile of each ring of the parametric model.

The cross-sectional profile is defined as r(u) where r is the radius between 0 and 1 and u is the circumferential coordinate, also between 0 and 1. Note that the profile is based on a unit circle with r=1. Referring to FIG. 6, the actual radius of the ring is not used until the design of the length profile. r(u) is defined by four parameters:

1. The number n of lobes. FIG. 6 on the right shows the cross-sections for n=0, 1, 2, 3. Higher values for n are supported in the model, but not commonly found in the colon.
2. The width w of each lobe, which is equal to 1-2·l with l as pictured in FIG. 6, defined as a fraction of the total circumference section, where the number of sections that make up the total circumference is the same as the number of lobes.
3. The concavity c of each lobe, defined as a fraction of the height h of the lobe. Note that h is not an independent parameter, but fully defined by w and n as:

$$h = 1 - \cos\left(\pi \cdot \frac{w}{\max(2, n)}\right) \quad (1)$$

4. The width t of the toe, i.e. the smooth transition region from the lobe to the outer circle, as a fraction of l.

Obviously, if n=0 then radius r(u)=1. The process for determining r(u) when n>1 is similar to when n=1, but repeated n times as u goes from 0 to 1. The only principle difference is that for n=1 there is by definition only 1 section which obviously takes up the entire circumference. However, a single lobe cannot take up more than half the circumference, otherwise r(u) could have more than 1 solution for certain u, but the toe is allowed to extend into the top half of the section. In other words, as the width is no more than 0.5, 1 is always at least 0.25 for n=1. To do the 2 lobe cross-section for example, we run the same procedure as for the 1 lobe cross-section, but only doing the bottom-half of the section, i.e. starting with u=0.25 and running to u=0.75 and then starting again at u=0.25 and again running to u=0.75. In this case l would be l' as pictured in FIG. 6. In general, for n lobes or sections, the 1 lobe procedure is repeated n times with u running from u=0.5−0.5/n to u=0.5+0.5/n each time and h scaled according to Eq. 1.

The length profile is defined as r(u,v) where r is the radius in meters and u and v are the circumferential and longitudinal coordinates as before, both between 0 and 1. Referring to FIG. 4(b), r(u,v) is defined by the cross-sectional profiles r(u) of the rings that make up the chamber, as determined before, and the following five parameters:

1. The actual radii of the start, middle and end rings in meters: $R_s$, $R_m$ and $R_e$ respectively.
2. The height FH of the folds, if present, defined as a fraction of the ring radius.
3. The sharpness FS or steepness of the folds, defined as larger than 0 (flat surface) and smaller than 1 (surface perpendicular to centreline).
4. The radius FR of the top of the fold or lobe, defined as a fraction of the ring radius.
5. The length L of the chamber in meters.

The process for calculating r(u,v) consists of four steps:
1. Calculation of a base radius based only on the longitudinal coordinate: r(v).
2. Calculation of the start (for v<0.5) or end (for v>0.5) ring and middle ring profiles $r_s(u)$ (or $r_e(u)$) and $r_m(u)$ respectively, based only on the circumferential coordinate u as described before, and weighing of $r_s$ and $r_m$ with W and (1−W) respectively, where the weight W is a function of v.
3. Multiplication of r(v) with the result from step 2.
4. Application of noise N (u,v) to obtain a more natural looking surface.

The base radius r(v) is a blend of the radii of the rings that make up the chamber. For v<0.5 it is a interpolation of the start ring and the middle ring, for v>0.5 it is an interpolation of the end ring and the middle ring. The process for v>0.5 is identical to that for v<0.5 but mirrored about v=0.5 and therefore omitted in the remainder of this description. To ensure a smooth transition from one chamber to the next, we define the tangent to the profile at v=0 and v=1 to be parallel to the centreline. This is achieved by using a third order function of v: $v^2 (3-2v)$ to interpolate between rings. This function of v is 0 for v=0, 1 for v=1 and its derivative or tangent is 0 at v=0 and v=1. Interpolation is now done in two steps. First, we interpolate between the start and end ring:

$$r(v) = R_s + (R_e - R_s) v^2 (3-2v) \quad (2)$$

Then we adjust this interpolation to ensure that $r(0.5)=R_m$, by applying an interpolation of the correction factor $\Delta R$, and obtain the base radius $r(v)$:

$$r(v)r(v)(1+\Delta R) \quad (3)$$

$$\Delta R = \left(\frac{R_m}{\frac{1}{2}(R_s + R_e)} - 1\right)\upsilon^2(3 - 2\upsilon) \quad (4)$$

where $\upsilon=1-2|\frac{1}{2}-v|$, i.e. $\upsilon=0$ for $v=0$ and $v=1$ and $\upsilon=1$ for $v=0.5$, hence $\upsilon^2(3-2\upsilon)$ provides a smooth interpolation going from 0 to 1 to 0 as v goes from 0 to 0.5 to 1, with a tangent of 0 at $v=0$, $v=0.5$ and $v=1$.

Next we calculate the relative ring radii $r_s(u)$ and $r_m(u)$ as described in the cross-sectional profile section and we weigh them with $W(v)$:

$$r_s(u)W(v)+r_m(u)(1-W(v)) \quad (5)$$

The weight $W(v)$ essentially defines the length profile of the chamber and is a non-linear function of v. From Eq. 5 it is clear that $W(v)$ provides a linear interpolation between the two rings, where at the start ring, when $v=0$, $W(v)$ will be 1, and at the middle ring, where $v=0.5$, $W(v)$ will be 0.

The final calculation of $r(u,v)$ is a simple matter of multiplying $r_v$ (Eq. 3) and $r_w$ (Eq. 5):

$$r(u,v)=r(v)r_w \quad (6)$$

To make the chamber look more natural, noise is applied in two ways. First of all, the circumferential profiles can be rotated about the longitudinal axis by adding an offset $\Delta u$ to u, and secondly, a two-dimensional noise function built from sin functions is applied:

$$r(u,v)=r(v)(r_s(u+\Delta u_s)W(v)+r_m(u+\Delta u_m)(1-W(v)))(1+N(u,v)) \quad (7)$$

where $N(u,v)$ is the noise function:

$$N(u, v) = \quad (8)$$

$$f_{0,0} \cdot \left(\sum_{i=1}^{n} f_{1,i}\sin(2\pi(i_{1,i}u + g_{1,i})) + \sum_{j=1}^{n} f_{2,j}\sin(2\pi(i_{2,j}v + g_{2,j}))\right) +$$

$$\ldots f_{0,1} \cdot (1 - 1) \cdot$$

$$\left(\sum_{k=1}^{n} f_{3,k}\sin(2\pi(i_{3,k}u + g_{3,k})) + \sum_{l=1}^{n} f_{4,l}\sin(2\pi(i_{4,l}v + g_{4,l}))\right)$$

in which the constants $f_{i,j}$ and $g_{i,j}$ are random values from the range 0 and 1, or from a subset of that range, and the constants $i_{i,j}$ are random integers, for example from the range 1 to 12. As can be seen in Eq. 8, the f's define the amplitudes, g's the phase offsets and i's the frequencies of the noise. The value I is the (normalised) amount of insufflation used in the chamber, allowing for additional noise representing chamber wrinkling when desufflating.

To increase the natural look of the chamber, the surface function $r(u,v)$ can be multiplied with a so-called bump map B:

$$r(u,v)r(u,v)\cdot(1+B_{scale}(B(u,v)+B_{offset})) \quad (9)$$

The bump map can be stored and queried as a texture on the graphics card, which minimised computation times as the graphics card is optimised for this type of process. The scale $B_{scale}$ could be made dependent on input parameters such as the colon insufflation. It would also be possible to combine multiple bump maps with the weight of each map again depending on input parameters.

The values of the parameters used in the parametric model are varied iteratively so that plausible (anatomically accurate) combinations of different parameter values are determined 302. The resulting multiple unique combinations of parameters are stored in database 204. Each combination of parameter models represents a different candidate.

From each unique combination of parameters, simulated image data is generated 304. That is, the values of the parameters are put into equations 1 to 9, which are solved by computer system 200 to produce a virtual three-dimensional mesh of a sub-part of the colon. A virtual camera is placed within this mesh having a particular location and orientation in relation to the centreline of the mesh, to generate an image that simulates what a camera during an endoscopy would capture of the interior of a chamber represented by that model and possibly some adjacent chambers.

The location and orientation of the camera are varied incrementally to create a set of images of the current combinations of parameters from multiple possible camera locations and orientations within the produced mesh. This is repeated for all parameter combinations determined at 302 to generate static simulated image data that represent within predetermined accuracy thresholds almost all the possible endoscopic views of the colon. The simulated image data is not of a specific case or person, rather the range of possibilities that are likely to be encountered during an actual endoscopy.

Figure 7A:
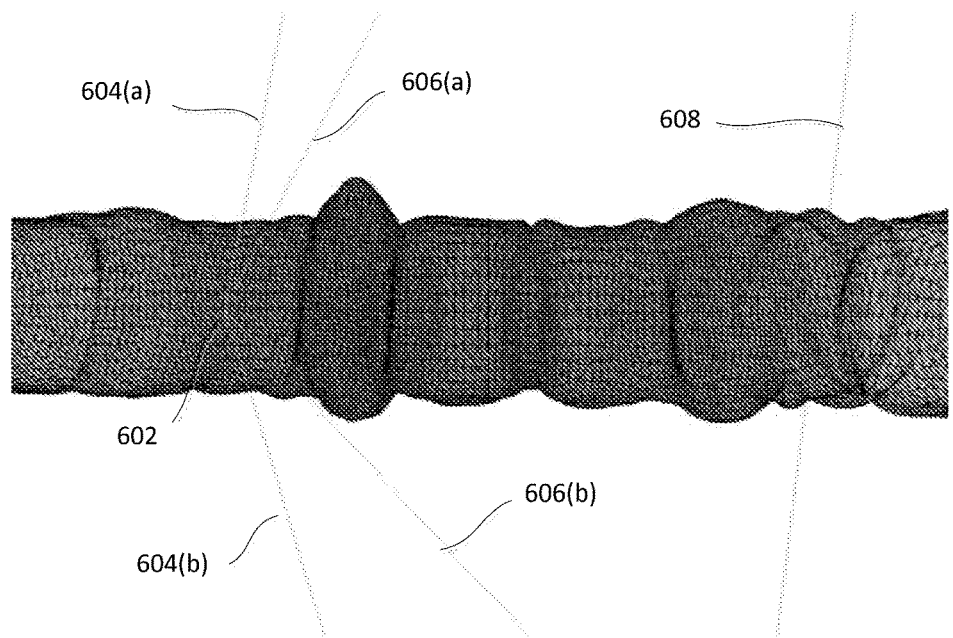
FIGS. 7 and 8 each illustrate a visual representation of parameter values of the parametric model and a visual representation of simulated image data based on the parameter values of the parametric model.
Figure 7B:
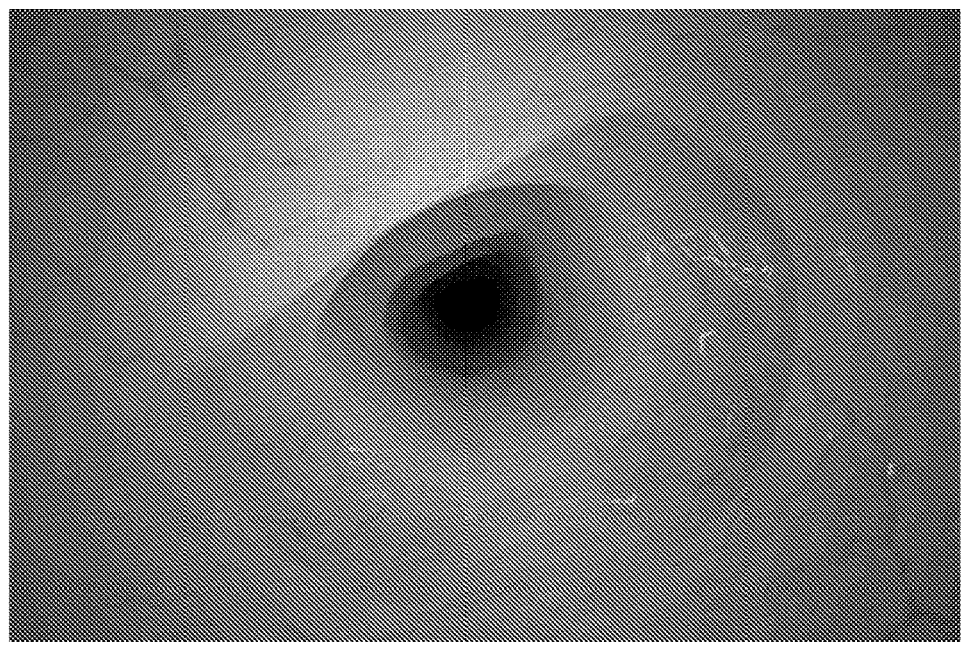

For example, the parameter combination of the model graphically shown in FIG. 7*a* results in a simulated image data as represented in FIG. 7*b*. The lines in FIG. 7*a* indicate the camera location and orientation. Point 602 indicates the camera location. Lines 604(*a*), 604(*b*), 606(*a*) and 606(*b*) indicate the edges of the camera's field of view and 608 indicates the maximum depth of the camera's view. That is, anything further along the colon past line 608 and away from the camera will appear black in FIG. 7*b*.

Figure 8A:
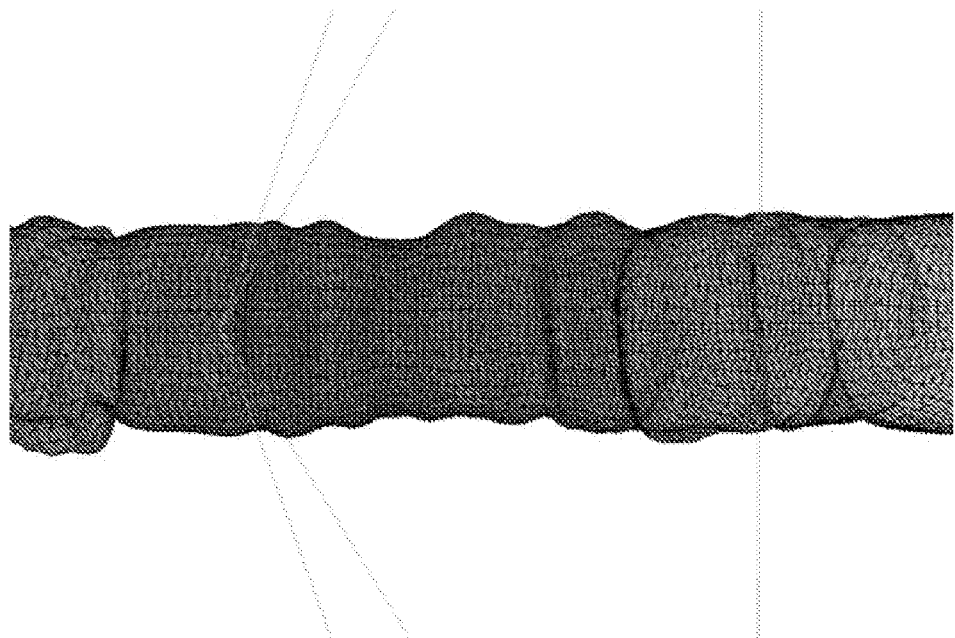
Figure 8B:
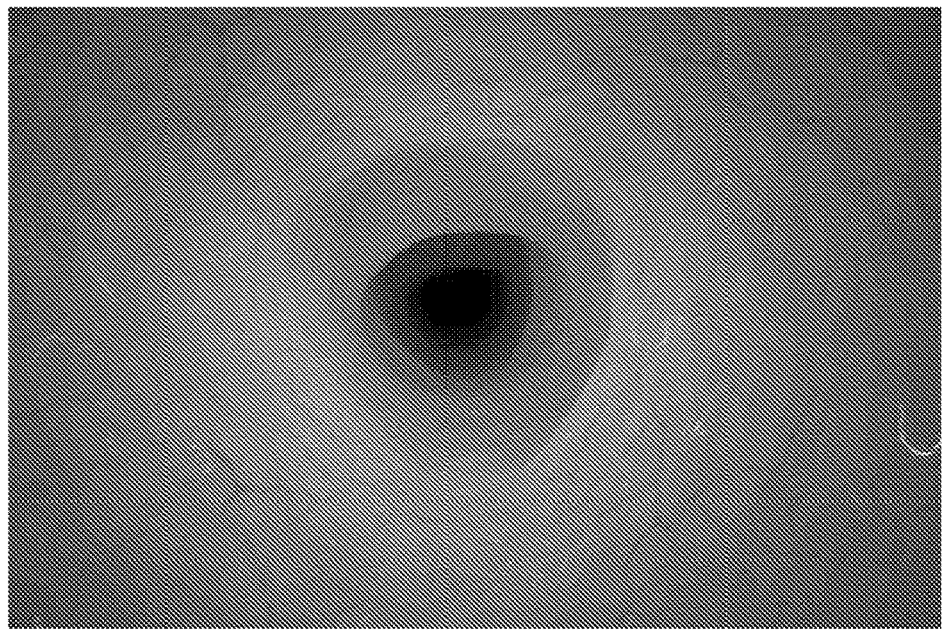

As a further example, the parameter combination of the model graphically shown in FIG. 8*a* results in simulated image data represented in FIG. 8*b*.

Next, each image is then analysed to determine 306 for each simulated image data a representation of distinguishing anatomical features or markers. The representation is a form that makes the use of the representation efficient for comparison. In this example, the representation is a feature vector.

Figure 9:
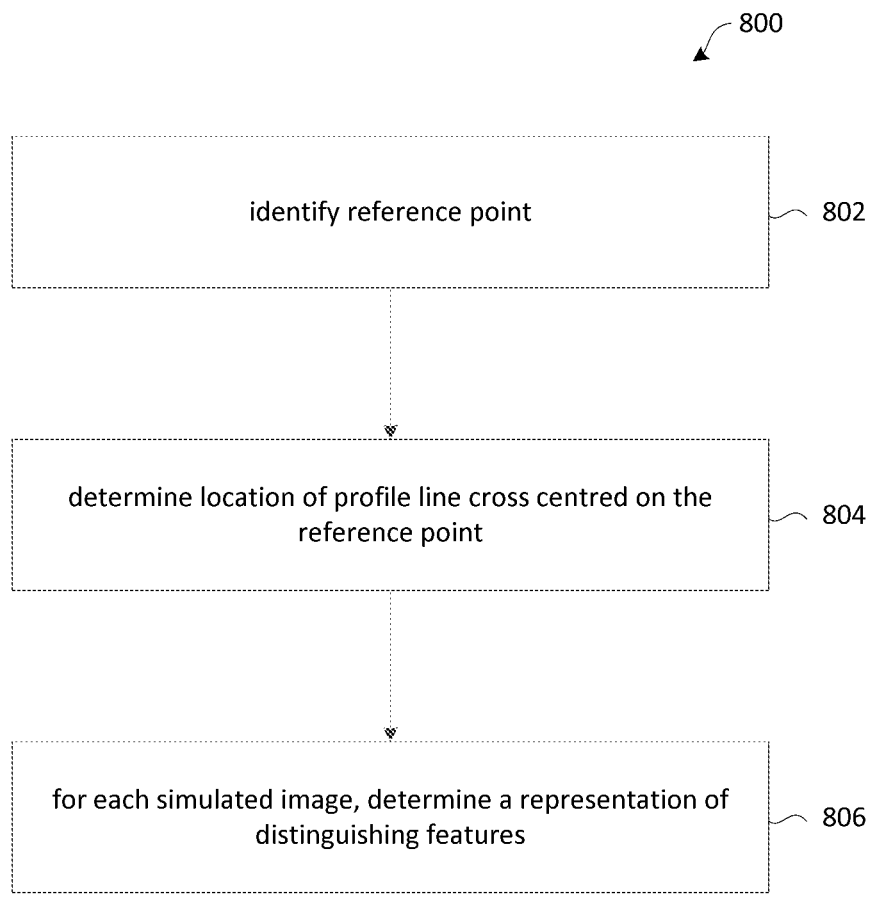
FIG. 9 is an example flow chart of the method for determining a representation of one or more distinguishing features of image data.
Figure 10:
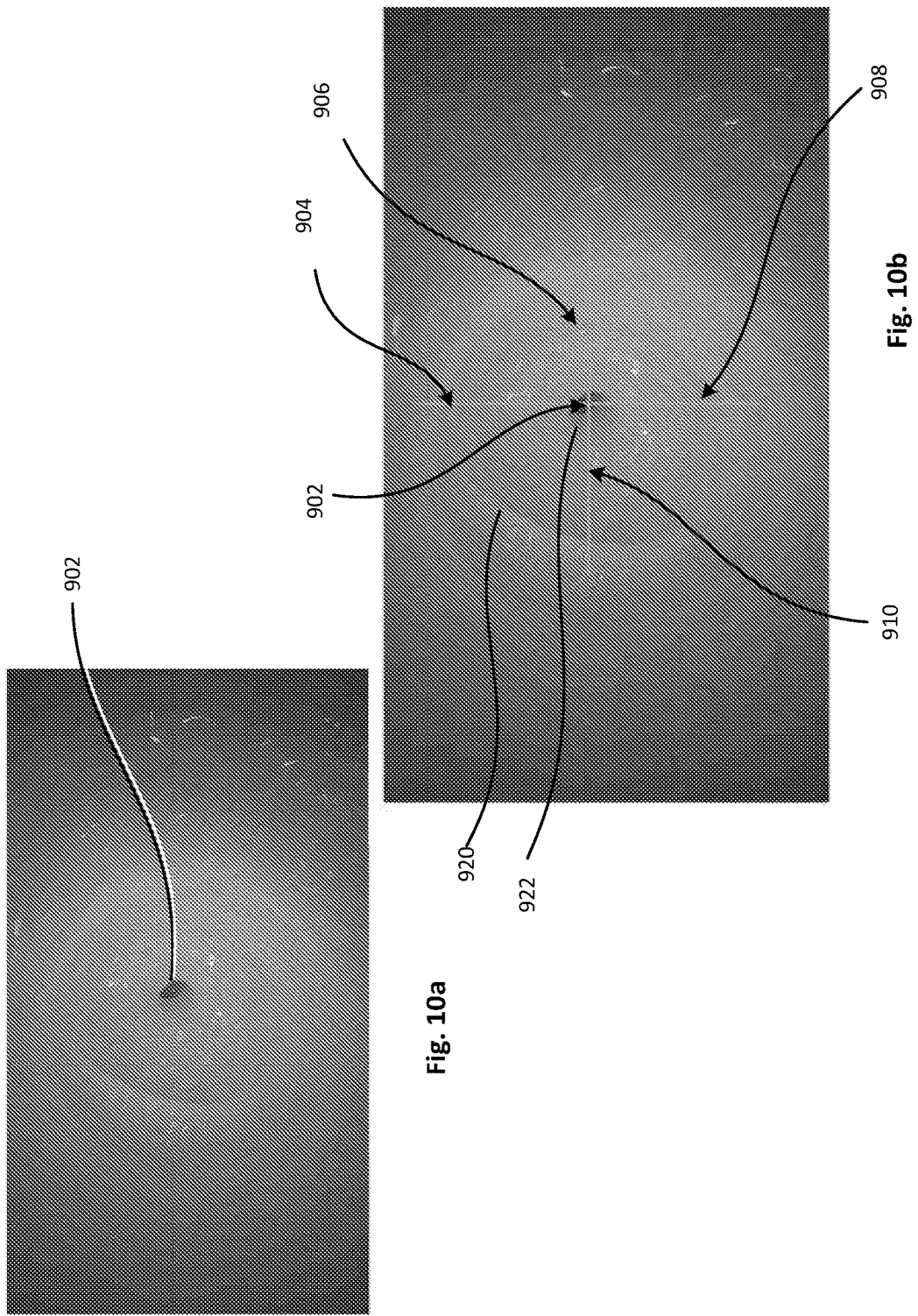
FIGS. 10 and 11 illustrates some examples of the steps of the method for determining a representation of one or more distinguishing features of an image of the colon.

The method of determining 306 a feature vector of a simulated image is now described with reference to FIGS. 9, 10 and 11.

The method 800 involves first identifying 802 a reference point in the image. The reference point can be determined using the darkest point of the image or by estimating the centre of mass. The centre of mass can be calculated by averaging the locations of the pixels with an intensity below a certain threshold. This threshold can be calculated by converting the image to greyscale and applying Otsu's method (see for example 'Automatic thresholding of grey level pictures using two dimension Otsu method', Jianzhuang et al, Circuits and Systems, 1991. Conference Proceedings, China). This method involves iterating through all the possible threshold values. For each of these threshold values the method calculates a measure of the spread for the pixel levels on each side of the threshold. The ideal threshold is the value that minimises the sum of spreads from each side of the threshold.

FIG. 10a shows a representation of example simulated image data with the reference point 902 identified.

Once the reference point 902 is determined, the location of lines extending from the reference point in a radial pattern can be determined 804. The number of lines is chosen to optimise the representation of distinguishing features. Referring to FIG. 10b, an example where the number of lines equals four can be seen resulting in horizontal 906 and 910 and vertical 904 and 908 lines forming the shape of a cross. These lines 904-910 represent profile lines and will be used to identify the relevant distinguishing features from the simulated image data.

In this example, the endoscope comprises a light source that emits light in the same direction as the view of the camera. As a result, since the surface normal of the haustral folds are almost parallel to the incidence of light, the reflection of the light is maximal and the brightest parts of the image represent the haustral folds. It may therefore be an advantage to use location of the haustral folds as the relevant distinguishing features, which are marked 920 and 922. In the image data representation, the haustral folds closer to the simulated camera position are further away from the reference point 902.

Figure 11:
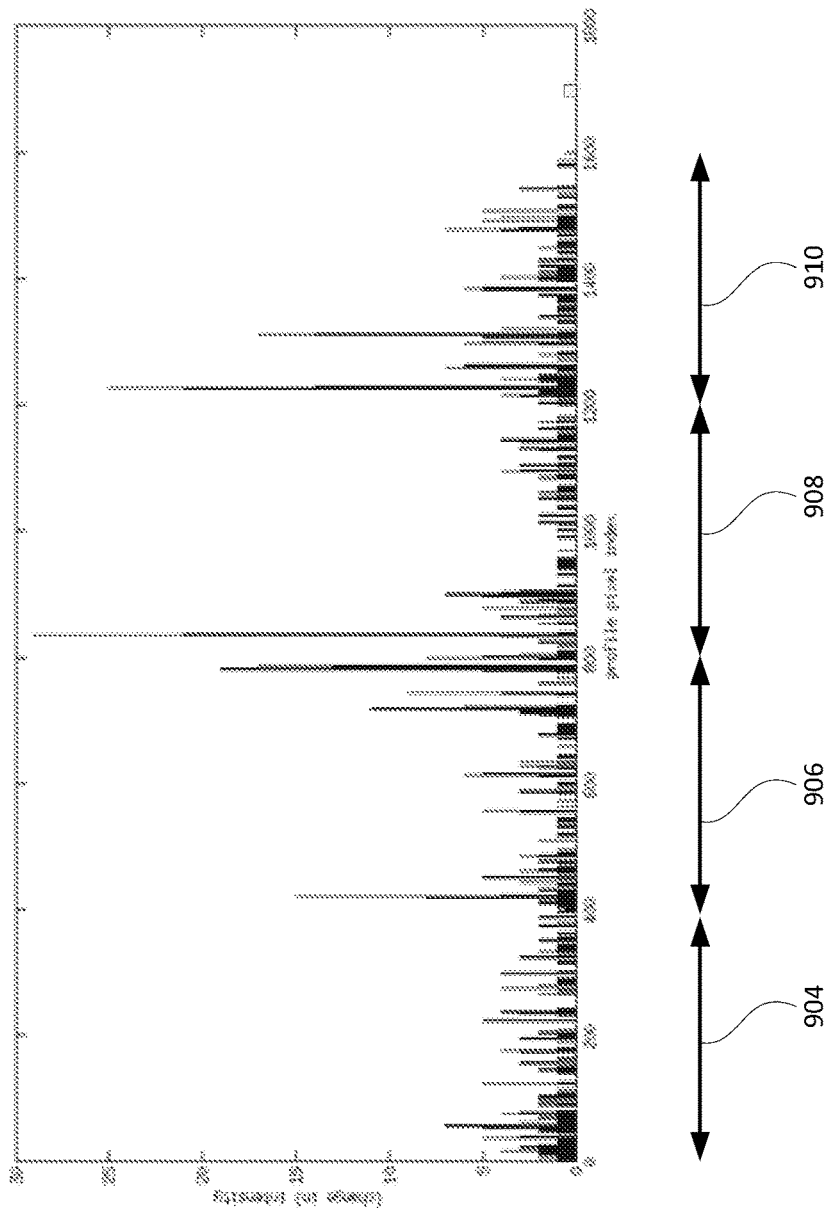

Vice versa, the longitudinal camera position relative to the natural folds is proportional to the location of the peaks along the horizontal axis in FIG. 11. This can be used as a first selection criterion for selecting the one of multiple candidates. More particularly, candidates where the closest haustral fold is at a different location than the location of the closest haustral fold in the captured image data can be disregarded in order to reduce the search space.

From the profile lines 904-910, a representation of the distinguishing features is determined 806, in this case a feature vector. The feature vector in this example is an array of quantitative measurements of the simulated image data. This feature vector is derived from the intensity of all the pixels that lie at the locations of the profile lines 904-910 when displayed with the lines. In this example, the feature vector is based on the intensity based value of pixels that are in an ordered sequence, first in order of the profile lines that the pixels belong to, and then the order that the pixels are located at the profile lines in relation to each other.

An example feature vector is shown graphically in FIG. 11 with the pixel of the profiles lines 904, 906, 908 and 910 are arranged on the x-axis and the y-axis showing the intensity based value of each pixel.

In this example, the y-axis presents the change in intensity. Intensity for a grayscale image is equivalent to how bright a given pixel is. In this example, useful quantitative measurements are the absolute intensity of each pixel. Or alternatively, the change in intensity (that is, relative intensity) between adjacent pixels can be determined. In this case the starting intensity value is taken from the pixel at the end of the profile lines 904, 906, 908, 910 at the centre of the cross and each adjacent pixel is taken as the next pixel along each profile line working to the end of relevant profile line. Change in intensity is important because a high value would indicate a strong probability that the pixel represents an edge of a haustral fold. Identifying haustral folds is useful as these folds provide a point of reference to match the image to a parametric model.

Any suitable method can be used to determine a representation of the distinguishing features of the image data. Trade-off between the richness of the features and computational time needs to be found. For example, all the pixels of the images are used as features, but this would results in large computation, which might not be feasible with today's computer. Various dimensionality reduction techniques can be apply such as principal component analysis, blocks optimisation, or wavelet filtering. The radial lines used in this application are one way to reduce the dimensionality of the feature space while keeping essential information able to match an image to candidates from the database.

This method 800 is repeated for every simulated image generated by training phase shown in FIG. 3. Each feature vector is also stored 308 in the database 204. As a result, each candidate stored in the in the database 204 is associated with one or more of:

(a) model details to generate the simulated image, including the unique combination of parameters for the parametric models of the visible chambers;

(b) camera details needed to generate the simulated image such as the location of the camera in three dimensional space and the orientation of the camera and the direction the camera is pointing, in relation to the centreline of the lumen represented in the simulated image data;

(c) one or more simulated images stored as simulated image data generated from the combination of parameter values; and (c) representation of one or more distinguishing features for that simulated image data.

As can be seen, the database 204 contains for each candidate information that is associated with unique simulated image data of the interior of the colon.

The candidates in the database 204 can be improved to support rotational invariance. In this case, when performing the method 800 of determining the feature vector of the simulated image data, the profile lines 904-910 are iteratively rotated slightly in the same direction about the reference point 902. In this case, the set of candidates stored in the database 204 comprise multiple candidates for a single set of geometric parameters where each candidate represents a different rotation angle. The larger the number of profile lines, the more invariant the testing method 208 is but is at the expense of a longer computation time.

Testing Phase

The testing phase of FIG. 2 will now be described in more detail.

During an endoscopy, video data is generated. This is usually done in a bronchoscopy by the insertion of a fibre optic camera and in a colonoscopy it is generally either a CCD or fibre optic camera.

The video is an aggregation of individual captured images, such as video frames. In a typical video, frames are typically acquired 25 times per second. This means the method 208 occurs cyclically every 40 ms. In this example the video would be analysed as the endoscopy is being performed in real-time, however it is to be understood that the video may be pre-recorded. Moreover, the method 208 need not be performed for every frame of an endoscopy video, this may be a result of not all frames being available or not useable due to occlusion or lighting. In other examples, not all frames are used in the method 208 to increase computational speed for real-time analysis. In this case, the selection of the number of frames to analyse is a balance of the computation time and accuracy.

The system 200 receives 210 each frame of the video as a static image.

Optionally, similarly to the method 800 described above, each frame is analysed to determine 211 a representation of the distinguishing features. The method is the same as the method described in relation to FIG. 9 and results in a representation of distinguishing features of the captured image. This feature vector is also stored in the database 202 associated with the relevant endoscopy image.

Then, for each image the sub-part of the lumen represented in the images is compared 212 to the entries in the database 204.

In the example, where the optional step 211 is performed, comparing 212 comprises comparing the feature vectors of the captured image data to the feature vectors of candidates stored in the database 204. That is, each of the entries in the database 204 that is a candidate is compared against the feature vector of the captured image. Comparison can be done for example through the determination of the Pearson product-moment correlation coefficient R of the two vectors. This results in a determination of the candidate that corresponds to the feature vector of the captured image data. For example, a correlation value for each entry in the database 204 can be determined. The higher the correlation value the closer the two images match. The entry in database 204 that has the highest correlation value is selected as the candidate that corresponds to the captured image, that is, the best match.

Figure 12:
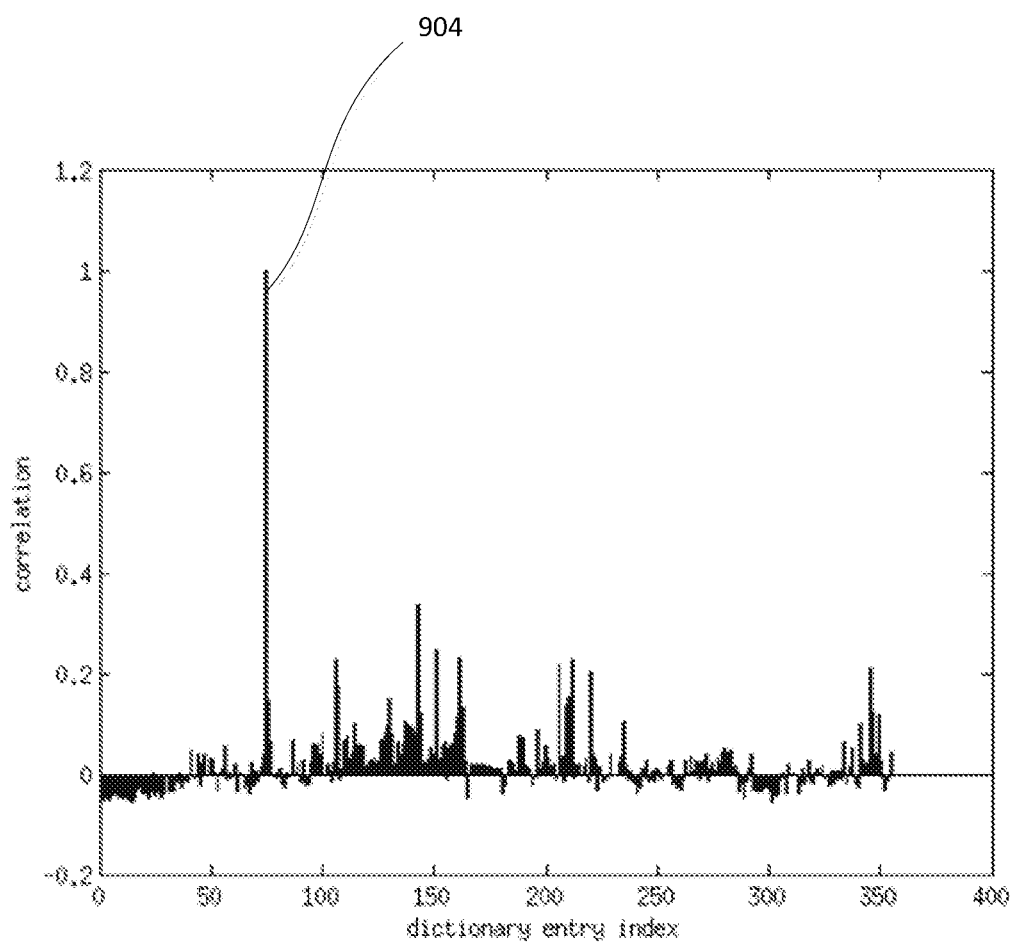
FIG. 12 graphically shows the result of an example comparison of captured image data to the multiple candidates.

FIG. 12 shows graphically this comparison of step 212, where every bar on the x-axis represents the correlation value of a different simulated image from the database 204. For ease of explanation, in this case the probe endoscopy image is actually a simulated image. The comparison of the image to itself results in a clear highest correlation value 904.

In other alternatives where the analysis of step 211 is not performed, the comparison 212 step compares the endoscopy image to each of the simulated images stored in the database 204 and in the same way determines a correlation value to then select the simulated image that has the highest correlation value as the candidate that corresponds to the captured image.

For every captured image data, the computer system 200 determines the corresponding candidate for the chamber that appears the largest and therefore in the best detail in the captured image data and stores 214 an association of the selected candidate with the captured image to represent the interior of the colon.

In one example, when a new video frame becomes available, the candidates are generated for that video frame, such as by selecting a sub-set of candidates from a larger set of candidates. This way, the search space can be constraint to only incremental changes between candidates selected for subsequent video frames, which can reduce computation time and stability of the selection process.

Further, the candidates may be arranged in a tree based structure. For example, the first branch in the decision tree may be the location of the haustral folds, such that only candidates are considered with similar location of those folds. Again, this can reduce the number of candidates to match the captured image against significantly.

In yet another example, a multi-scale approach may be used. Each candidate may be stored in different levels of detail, such that coarser versions represent a range of model parameters. A first matching step selects a coarse estimate of the parameters and then the captured image is matched against finer versions. In the example of FIG. 11, at the first level of refinement, one hundred pixels may be averaged such that the feature vector comprises only four values. Once a corresponding coarse candidate is selected, finer versions of that candidate become available for further matching.

Storing the association may comprise storing the parameter values of the identified candidate or storing an identifier, such as index, of that candidate together with a pointer to the captured image or storing a pointer in the data structure of the captured image to the parameter values of the candidate.

Further estimates for the candidate for the rest of the chambers of the colon that are visible in the captured image data are also determined. These are considered simply estimate as further detail of these chambers will become visible in subsequent images that will allow the estimate of the selected candidate to be updated and typically made more accurate.

In another example, where the video data is generated while the endoscope is pulled back through the colon, the first video image may not show any subsequent chambers. As the camera travels backwards more of the current chamber becomes available and a corresponding candidate can be selected for each image of the video. Ideally, the candidates should only differ in the location of the camera and not in the geometric parameters of the model. This way, the selection of the candidate can be refined. When a brightness peak is detected on the pixels at the end of the radial lines, this indicates that a haustral fold is visible and the camera has reversed into a new chamber. At this point the geometric parameters of the first chamber may be frozen since it is unlikely that more information will be gathered about that chamber since the camera is now in a different chamber. In this example, the system 200 may select candidates based on only those pixels that are closer than the closest brightness peak, that is, pixels relating to the current chamber.

In this example, the haustral lines may also be associated with a unique identifier, such as a counter. As a result, the location of the camera within the colon is available, similar to a street number of a postal address.

Using this sequence of candidates, a model underlying the three dimensional representation of the entire colon can be determined as the endoscope inspects the colon.

The generated model can be used for assisting a surgeon in real time, for navigating, and also for reporting on features of the endoscopic procedure. For example, the model can be used to estimate areas that might have been missed, which can then be reported by identifying that part of the model that had not been in the camera field of view.

The generated model can further be associated with patient 104 and stored in database 204 or a separate database. This allows the generated model to be used at a later date, for example if patient 104 returns for a second colonoscopy. In this way the stored generated model can be accessed from the database and the parameters of the model can be adapted to the second colonoscopy. This prevents having to generate a new three dimensional representation of the colon for patient 104, as it is assumed that the colon would not have significantly changed between adjacent colonoscopies. This is an advantage of the disclosure as it potentially saves time and resources.

Figures 13A, 13B:
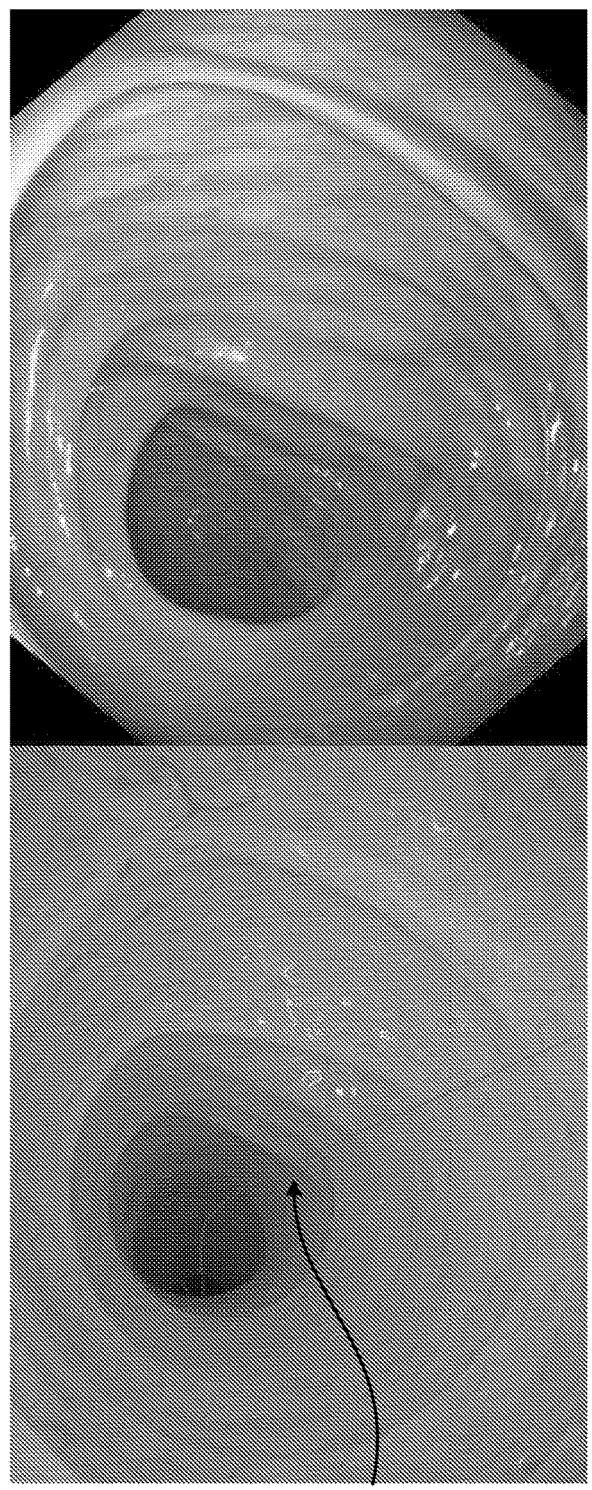
FIG. 13 compares example captured image data taken during an endoscopy to the selected corresponding simulated image data.

FIG. 13 shows a comparison between captured image data as seen in FIG. 13b and the simulated image data that has the highest correspondence in FIG. 13a. The simulated image data is the simulated image associated with the feature vector that best matched the feature vector of the captured image data. This side-by-side display of the endoscopy image and the matching simulation image can be displayed to the surgeon on a display 207 in communication with the computer 200.

Computer Hardware

Figure 14:
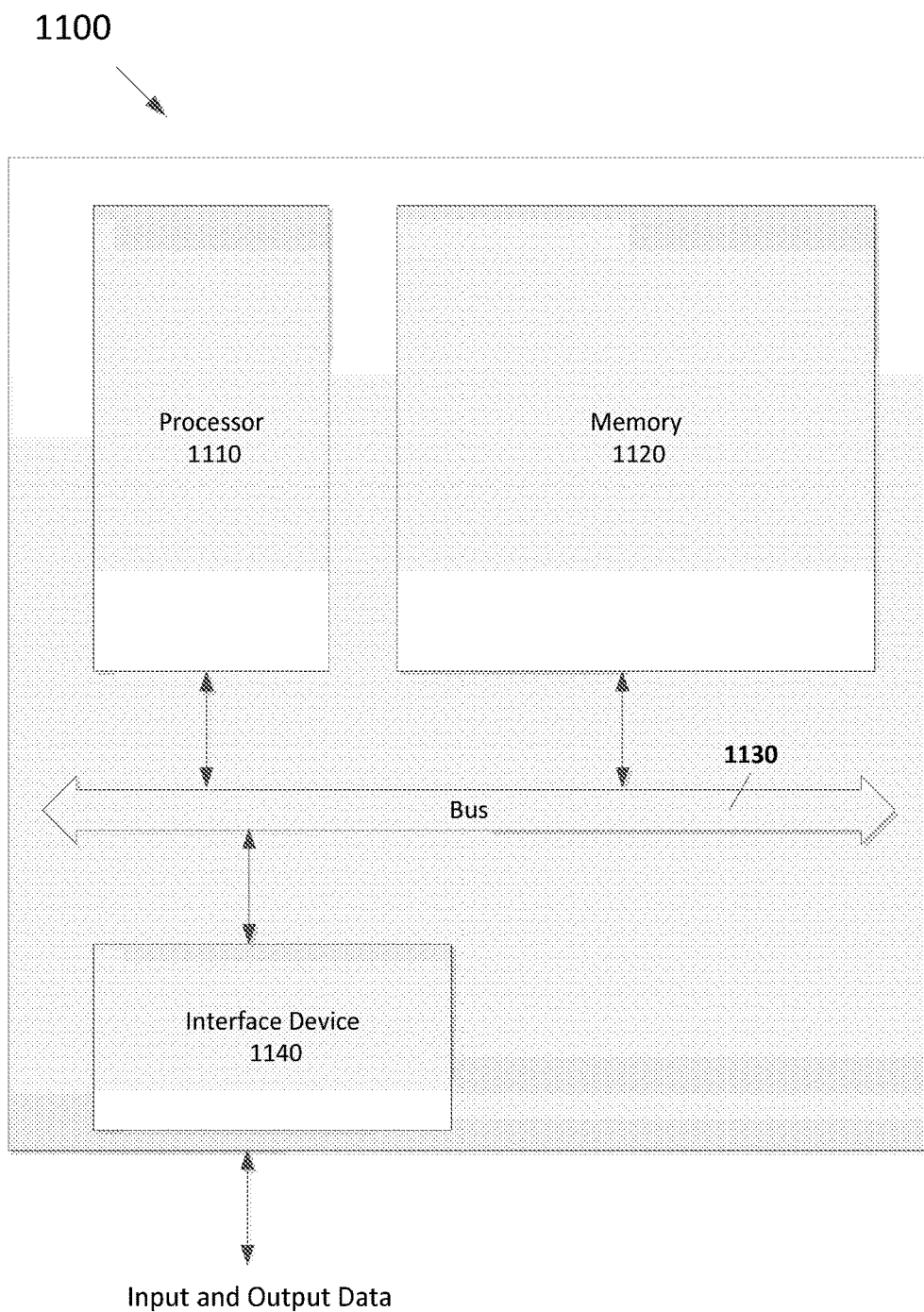
FIG. 14 is more detail of an example computer system that can perform the method described above.

FIG. 14 is a diagram illustrating a computer system 200 for representing an interior of a lumen.

The computer system 1100 includes a processor 1110, a memory 1120, a bus 1130 and an interface device 1140. The processor 910, the memory 920 and the interface device 940 communicate with each other via the bus 1130.

The interface device 1140 interfaces with other devices for example a camera to receive one or more images representing a sub-part of a lumen. The image data may be communicated to the memory 1120 via the bus 1130.

Software being instructions to allow the computer 1100 to perform the methods of FIG. 2 and optionally FIG. 3 are stored in memory 1120.

The memory 1120 may store the databases 202 and 204, or in other examples the databases may communicate via the interface 1140 to retrieve the relevant data from databases 202 and 204 as required, and store data such as the determined feature vectors and correlation values to the databases 202 and 204.

Camera Variations

Differences in the video frames occur with camera variations during an endoscopy. A slight change in the camera position and orientation can lead to a significantly different view of the same sub-part of a lumen being represented in the image. In turn, the determined feature vector is also significantly different even though they both represent the same shape of an interior of sub-part of a lumen.

Not all camera changes lead to different feature vectors as the reference point 902 described earlier is used to place the profile lines since the method is translationally invariant. For example, if there are two images that are identical apart from one being shifted moderately in a horizontal and/or vertical direction, the process will produce identical feature vectors for these images since both images will use the same reference point.

If there is a substantial shift such that the reference point is too close to the edge of the image, then some of the profile lines are cut short by the image edge. This would result in reduced profile lines, and therefore reduced feature vectors. This in turn reduces the confidence in any found match, and may lead to multiple matches in the database if the matched entries only differ in the part of the image that was excluded because it was not available in the image being tested.

In instances where part of the camera image is obstructed, for example because of dirt or water on the camera lens, this can also cause the profile lines to be cut short.

Making the comparison 212 rotationally invariant is described above by rotating the cross of the profile lines 904-910 as described above.

Additionally, the feature vector comparison 212 can be made affine invariant. That is, the feature vector is affine invariant if the coordinate system it is represented in can change without affecting the relative geometry of the vector. The camera position and orientation are calculated relative to the centre line of the lumen. For each captured image, a comparison can be made between all the pixels in the given image and the previous captured image of the video. Based on this comparison the motion of the camera is detected. Given that the lumen has the calculated geometry from the selected candidate and knowing the camera displacement, the position and orientation of the camera relative to the colon can be estimated accurately in the current captured image data. A cylindrical approximation of the colon is superimposed over the image using the reference points calculated above to fix the position. From this cylindrical approximation, the longitudinal lines of the cylinder can be used as profile lines. Further, the centre line is used to project a cylinder in the camera view. The profile lines of the feature vector are then aligned and scaled according to the projection lines of the cylinder.

Figure 15:
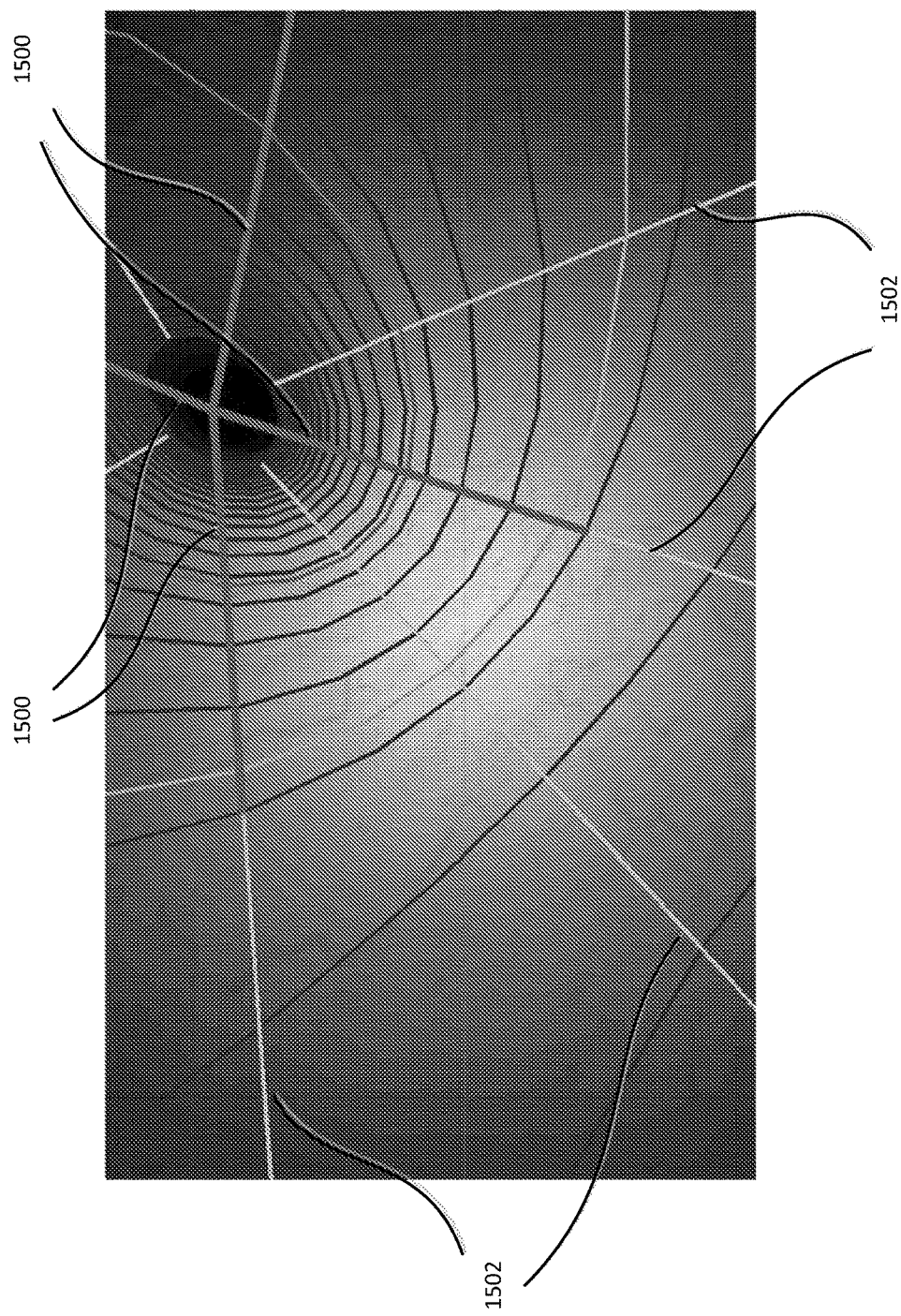
FIG. 15 is an example schematic representation of a projection of a cylinder aligned with the centre line of the lumen.

FIG. 15 contains a projection of a cylinder aligned with the centre line of the lumen. The lines 1500 are the profile lines. These are aligned and scaled onto the lines 1502 of the cylinder.

Accuracy can be improved by the following. Once the simulator parameters are obtained, they can be varied slightly in numerous ways to generate new simulated images. The feature vectors for each of the simulated images can be recalculated and added to a dynamic database along with the corresponding simulator data. The query image is then tested against these new images This process can be repeated until the desired accuracy is achieved.

Reducing Comparison Computation

It is very likely that consecutive frames will show very similar or even identical views of very similar or even identical geometry. Hence, once the process has positively matched a frame to a candidate, the next frame may not need to be tested against the whole database. It may only need to be tested against a subset of the candidates similar to the estimates made from the previous frame. The aim is to refine only the estimates. Alternatively, a dynamic set of candidates can be generated for the next frame. This can be continued for consecutive frames until the best correlation drops below a threshold of minimum acceptance, in which case the search can be expanded to a larger subset candidates, or to the whole database.

Other Volumes

Bronchi differ from a colon in that the bronchi branch into smaller bronchioles which are smaller tubes. For the most of the navigation of the bronchi there is a single entry point into a subsection of the lumen (main trunk) and two, three or four exit points into smaller child branches. This branching adds a level of complexity as the number of conceivable shape variations in an image, and therefore the number of entries in the database, is proportional to the number of branches visible in the image.

Figure 16:
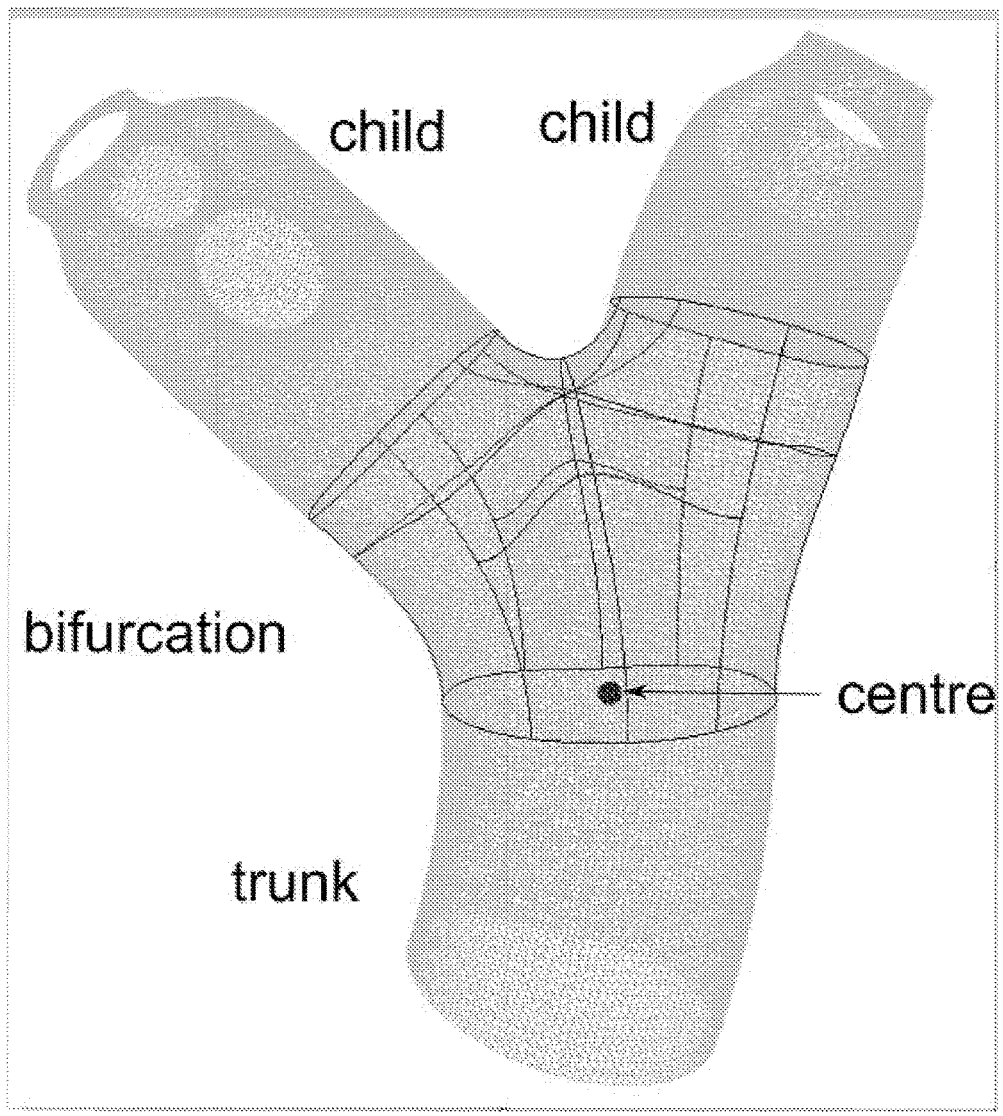
FIG. 16 is an example representation of a bronchi mesh.

A parametric model of a bronchus and its bifurcation into two or more branches can be used in this method. Again this parametric model can be used to generate meshes of the surface of any conceivable shape of a complete set of lungs. FIG. 16 shows one of these bronchus meshes consisting of a main trunk (lumen) and a bifurcation of the lumen into two child branches. By varying the parameters used to generate this bronchus shape, a database associated with simulated image data of different lung parts can be built up and used for matching of images from bronchoscopy.

In the bronchi example, the child branches will each have an opening with diameters, eccentricity and relative position to each other. This information can be combined to build a complete bronchial tree.

For example during a bronchoscopy, the endoscope has to navigate a tree of branches which is challenging to do. A three dimensional representation is generated and is able to show where the endoscope is located to help the clinician navigate the bronchi tree.

Even anatomy that are not made of lumen such as laparoscopy can be simulated. In fact any volume of the body represented using a parametric model and captured images. This could be useful for laparoscopic intervention of the prostate or for future robots to navigate in the body.

Converting to 2D Image

Once a captured image data is matched to a candidate in the database 204 image 302, the associated camera and model parameters 301 can be used to recreate the three-dimensional shape visualised by the computer 200 as a two-dimensional image 302 that resembles the query image. By inverting this visualisation process every pixel in the query image can be mapped to a three-dimensional location. This location can be expressed in Cartesian coordinates (x,y,z) but also in any other type of three-dimensional coordinate system, such as a cylindrical coordinate system (u,v,r) wherein u is the radial or circumferential coordinate, v is the longitudinal coordinate along the centre line of the lumen, and r is the distance of the point to the centre line.

The process described above may be performed for most or all images 402 as they are continuously being obtained from endoscopic video. Many of these consecutively or non-consecutively obtained images may provide information that overlaps information derived from previous images. This overlap can be used to merge the three-dimensional shapes into a three-dimensional representation of the complete lumen.

In some occasions the overlapping information can be contradicting: when the same location/pixel is seen on two or more frames. When merging the information, each bit of information may be weighted for relevance based on a number of criteria, such as distance to the camera when the information was obtained and time lapsed since the information was obtained. The latter is relevant as the colon is not a static object and hence older information may not reflect the current shape of the colon. Information with a higher weight will be more dominant when merging contradictory information into a three-dimensional shape.

Figure 17:
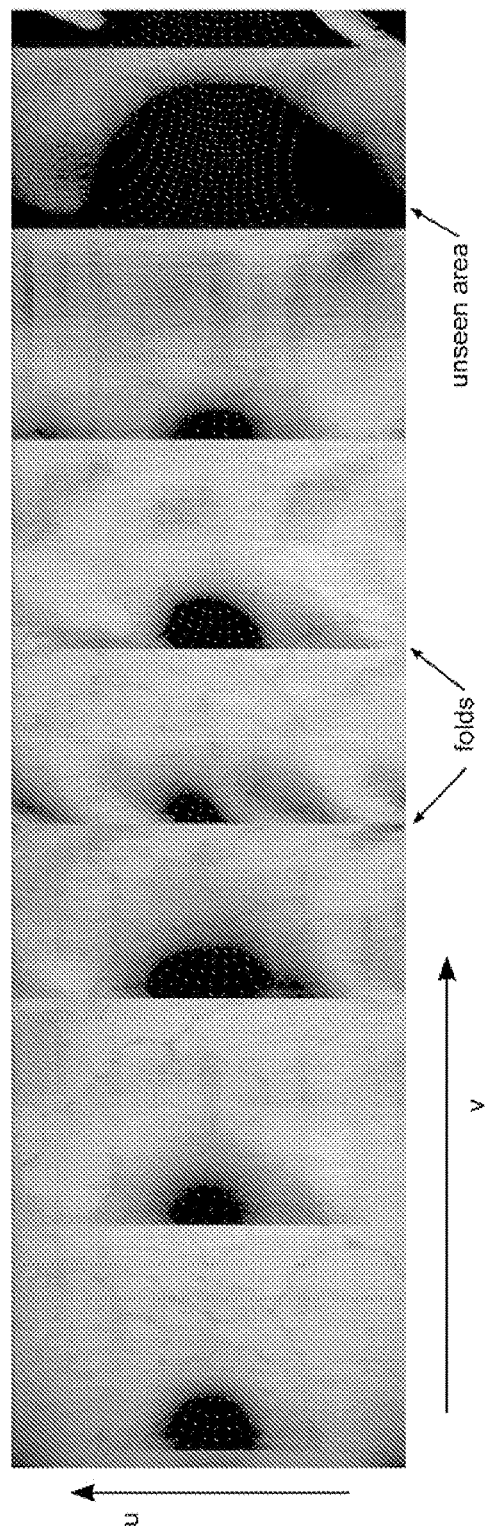
FIG. 17 is an example of the two-dimensional image of the colon surface that is generated from the three-dimensional captured data.

Once the image or images have been matched and a merged three-dimensional shape has been generated a number of deductions can be made. An opened-up, flattened image of the colon surface can be generated by taking the cylindrical coordinate system (u,v,r) mapping and plotting it as a two-dimensional map with u and v and the vertical and horizontal pixel coordinates, see FIG. 17. In this map, haustral folds show up as vertical lines, as each fold defines the edge of a chamber and hence every point on a fold will have the same longitudinal (v) coordinate. Also, areas to which nothing has been mapped will show up as black, indicating areas of the lumen that have been missed by the camera. This and other important medical diagnostic information can be made available to the operator of the endoscopy. Other information relating to the endoscopy such as the internal surface of the lumen and camera movement can be estimated. For example, the practitioner can continuously observe the black areas and steer the endoscope to these areas with the aim to eliminate all black areas such that as much as possible of the colon is inspected.

Database Design Alternatives

Each candidate entry in the database 204 may contain the feature parameters of the parametric model, camera information, the simulated image and feature vector described in relation to FIG. 3 and FIG. 8 provided that the comparison 212 of the method 208 can be performed and/or the entry contains links to other entries that share identical features, such as identical parameters or camera information.

Further the database, may be structured in any suitable way, such as distributed over many databases typically to assist with efficiency. For example the unique combinations of parameters of the parametric model may be stored in one database, where in a second database the multiple rotationally invariant feature vectors associated with the same parameters of the parametric model by a link to the first database. In further examples, unique combinations of parameters of the parametric model may be stored in one database, where in a second database all variations in camera details, which combined with the same parametric model lead to different feature vectors, may be stored.

Further, the databases 204 and 202 may be distributed, may be remote or local to the computer 200 and may be combined into a single database. The databases 202 and 204 may form part of a database management system.

While some of the above examples refer to the interior of the colon the method is applicable to represent the interior of any volume that can be represented by simulated image data. One example volume is a lumen. In medical terms a lumen is the inside space, such as a cavity or channel, of a component or structure of the body. Examples of lumens are the colon, the pathways of the bronchi in the lungs and blood vessels.

It should be understood that the techniques of the present disclosure might be implemented using a variety of technologies. For example, the methods described herein may be implemented by a series of computer executable instructions residing on a suitable computer readable medium. Suitable computer readable media may include volatile (e.g. RAM) and/or non-volatile (e.g. ROM, disk) memory, carrier waves and transmission media. Exemplary carrier waves may take the form of electrical, electromagnetic or optical signals conveying digital data steams along a local network or a publically accessible network such as the internet.

It should also be understood that, unless specifically stated otherwise as apparent from the following discussion, it is appreciated that throughout the description, discussions utilizing terms such as "receiving" or "obtaining" or "determining" or "sending" or "mapping" or the like, refer to the action and processes of a computer system, or similar electronic computing device, that processes and transforms data represented as physical (electronic) quantities within the computer system's registers and memories into other data similarly represented as physical quantities within the computer system memories or registers or other such information storage, transmission or display devices.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

The invention claimed is:

1. A computer implemented method for representing an interior of a lumen, comprising:
   receiving captured image data of the interior of a subpart of the lumen;
   generating multiple candidates, each candidate representing combination of parameters of a parametric model of a sup-part of the lumen;
   generating simulated image data for each of the multiple candidates, the simulated image data representing the interior of a sub-part of the lumen based on the parametric model;
   selecting one of multiple candidates that corresponds to the captured image data by comparing the representation of one or more distinguishing features of the captured image data to the simulated image data for each of the multiple candidates; and
   storing an association of the selected one of the multiple candidates with the captured image data to represent the sub-part of the lumen.

2. The computer implemented method according to claim 1, wherein the candidate is associated with a representation of one or more distinguishing features of the simulated image data.

3. The computer implemented method according to claim 2, wherein the candidate is associated with multiple representations of the one or more distinguishing features.

4. The computer implemented method according to claim 2, wherein the parametric model is cylindrical, such that the representation of the one or more distinguishing features of the simulated image data is invariant to one or more of orientation and translation.

5. The computer implemented method according to claim 2, wherein selecting one of the multiple candidates comprises comparing the representation of one or more distinguishing features of the captured image data to the representation of one or more distinguishing features of the simulated image data of each the multiple candidates.

6. The computer implemented method of claim 1, wherein the stored association of the one of the multiple candidates with the captured image data comprises storing a copy of or pointer to parameters of the model.

7. The computer implemented method according to claim 1, wherein selecting one of the multiple candidates comprises initially:
selecting one of multiple intermediary candidates, each intermediary candidate being associated with simulated image data of a sub-part of the interior of the lumen such that the selected one of the multiple intermediary candidates corresponds to the captured image data; and
determining the multiple candidates based on the selected one of the multiple intermediary candidates;
wherein the selected one of the multiple candidates corresponds to the captured image data by having greater similarity with the captured image data than compared to similarity of the selected one of the multiple intermediary candidates to the captured image data.

8. A non-transitory computer-readable medium, including computer-executable instructions stored thereon that when executed by a processor causes the processor to perform the method of claim 1.

9. A computer system to represent an interior of a lumen, the computer system, comprising:
an input port to receive captured image data of the interior of a sub-part of the lumen;
a processor configured to:
generate multiple candidates, each candidate representing a combination of parameters of a parametric model of a sub-part the lumen;
generate simulated image data for each of the multiple candidates, the simulated image data representing the sub-part of the interior of the lumen based on the parametric model; and
determine a representation of one or more distinguishing features of the captured image data;
select one of multiple candidates that corresponds to the captured image data by comparing the representation of one or more distinguishing features of the captured image data to the simulated image data for each of the multiple candidates; and
memory to store an association of the selected one of the multiple candidates with the captured image data to represent the interior of the sub-part of the lumen.

\* \* \* \* \*